United States Patent
Inwald et al.

(10) Patent No.: US 12,009,109 B2
(45) Date of Patent: Jun. 11, 2024

(54) SMART DOSING FOR CANCER THERAPY

(71) Applicant: OptimDosing LLC, Farmington Hills, MI (US)

(72) Inventors: David Inwald, Berkley, MI (US); Kenneth I. Kohn, West Bloomfield, MI (US)

(73) Assignee: OptimDosing LLC, Farmington Hills, MI (US)

( * ) Notice: Subject to any disclaimer, the term of this patent is extended or adjusted under 35 U.S.C. 154(b) by 164 days.

(21) Appl. No.: 17/127,352

(22) Filed: Dec. 18, 2020

(65) Prior Publication Data

US 2021/0193332 A1 Jun. 24, 2021

Related U.S. Application Data

(60) Provisional application No. 62/949,537, filed on Dec. 18, 2019.

(51) Int. Cl.
  *G16H 70/40* (2018.01)
  *A61K 45/06* (2006.01)
  (Continued)

(52) U.S. Cl.
  CPC ............ *G16H 70/40* (2018.01); *A61K 45/06* (2013.01); *G16H 10/60* (2018.01); *G16H 20/10* (2018.01); *G16H 20/60* (2018.01); *G16H 70/20* (2018.01)

(58) Field of Classification Search
  CPC ........ G16H 10/00; G16H 10/60; G16H 20/00; G16H 20/10; G16H 70/20; G16H 70/40;
  (Continued)

(56) References Cited

U.S. PATENT DOCUMENTS

2004/0121305 A1* 6/2004 Wiegand ............ G01N 33/5091
  435/4
2004/0193019 A1* 9/2004 Wei ........................ G16H 50/70
  600/300
(Continued)

FOREIGN PATENT DOCUMENTS

| WO | WO-0004194 A1 * | 1/2000 | ............ C12Q 1/6883 |
| WO | WO-0223186 A2 * | 3/2002 | ............. G01N 33/48 |
| WO | WO-2016139534 A2 * | 9/2016 | ......... G06F 19/3456 |

OTHER PUBLICATIONS

Basch, Ethan; Methods for Implementing and Reporting Patient-reported Outcome (PRO) Measures of Symptomatic Adverse Events in Cancer Clinical Trials; Clinical Therapeutics 38.4: 821-830. Elsevier Limited. (Apr. 2016) (Year: 2016).*

*Primary Examiner* — Hiep V Nguyen
(74) *Attorney, Agent, or Firm* — Kohn & Associates PLLC (57) ABSTRACT

A method of dosing cancer therapies, by collecting patient data including cancer therapies/drugs to be taken, analyzing the data in view of dosing criteria established based on outside data, and determining a dose for each cancer therapy/drug taken. A logic engine for dosing cancer therapies, including an algorithm stored on non-transitory computer readable media for collecting clinical trial data to establish criteria for dosing cancer therapies/drugs to a single patient and patient data and storing the clinical trial data and patient data in a database, analyzing the patient data in view of criteria established from the clinical trial data, and determining a dose for each cancer therapy/drug. A method of adjusting treatment of a cancer patient.

16 Claims, 6 Drawing Sheets

(51) Int. Cl.
    *G16H 10/60*    (2018.01)
    *G16H 20/10*    (2018.01)
    *G16H 20/60*    (2018.01)
    *G16H 70/20*    (2018.01)

(58) Field of Classification Search
    CPC ........ G16H 20/60; G16H 70/00; A61K 45/00; A61K 45/06
    USPC .......................................................... 705/3
    See application file for complete search history.

(56) References Cited

U.S. PATENT DOCUMENTS

| | | | | |
|---|---|---|---|---|
| 2006/0235881 | A1* | 10/2006 | Masarie | G16H 20/10 |
| 2008/0008991 | A1* | 1/2008 | Groen | G16H 20/10 |
| | | | | 435/5 |
| 2009/0167531 | A1* | 7/2009 | Ferguson | G16H 40/67 |
| | | | | 340/572.1 |
| 2010/0099087 | A1* | 4/2010 | Stanton, Jr. | C12Q 1/6886 |
| | | | | 435/29 |
| 2015/0025394 | A1* | 1/2015 | Hong | A61B 5/02427 |
| | | | | 600/479 |

\* cited by examiner

SMART DOSING FOR CANCER THERAPY

BACKGROUND OF THE INVENTION

1. Technical Field

The present invention relates to methods of determining dosing of cancer therapies. More specifically, the present invention relates to methods, software, and algorithms for determining single and multiple drug doses for an individual patient or a patient population based on compilation and analysis of clinical study data.

2. Background Art

Many individuals, especially as they age, need to take multiple drugs for different indications. Taking multiple drugs comes with risks, because drug interactions can cause unwanted and harmful side effects, and even cognitive side effects that can impact daily activities. In the time period of 2011-2014, the CDC states that 23.1% of individuals used three or more prescription drugs in the past 30 days, and 11.9% used five or more prescription drugs in the past 30 days. Over 40% of individuals over 65 years old are taking five or more drugs daily. Many individuals who also decide on an appropriate dose for themselves (such as increasing a dose) without doctor input can also inadvertently cause a reaction with other drugs that they self-administer. Even doctors may not be aware of drug interactions, and it is usually up to the individual to ask a pharmacist of any potential problems. Many individuals also take over-the-counter drugs, vitamins, and supplements without thinking that they may have an impact on each other and/or on prescription drugs.

Quinn, et al. (Sci. Data. 2017; 4: 170167) states that half of patients taking prescription drugs are taking two or more, and 5% take eight or more, and most multidrug combinations are used for treating metabolic syndrome. Quinn, et al. studied insurance claims to determine the number of prescription drugs patients are taking within a 30 day window that overlap. Table 3 in Quinn, et al. details the 3-drug combinations that are most represented prior to emergency department visits. Table 4 details the most common and overrepresented drug ingredient co-exposures with metformin or oxycodone.

Online drug interaction checkers exist, such as Drugs-.com, and websites like these can provide warnings of interactions with a drug that an individual is taking. A list of side effects is generated for each combination of drugs. However, there is no information as to whether a particular dose causes an effect, or what dose the individual should take based on the combination of drugs that the individual is already taking.

U.S. Pat. No. 6,658,396 to Tang, et al. discloses neural networks that are trained on historical data, and used to predict any of (1) optimal patient dosage of a single drug, (2) optimal patient dosage of one drug in respect of the patient's concurrent usage of another drug, (3a) optimal patient drug dosage in respect of diverse patient characteristics, (3b) sensitivity of recommended patient drug dosage to the patient characteristics, (4a) expected outcome versus patient drug dosage, (4b) sensitivity of the expected outcome to variant drug dosage(s), (5) expected outcome(s) from drug dosage(s) other than the projected optimal dosage. Both human and economic costs of both optimal and sub-optimal drug therapies may be extrapolated from the exercise of various optimized and trained neural networks. Heretofore little recognized sensitivities—such as, for example, patient race in the administration of psychotropic drugs—are made manifest. Individual prescribing physicians employing deviant patterns of drug therapy may be recognized. Although not intended to prescribe drugs, nor even to set prescription drug dosage, the neural networks are very sophisticated and authoritative "helps" to physicians, and to physician reviewers, in answering "what if" questions. However, Tang, et al. cannot analyze multiple drugs in combination.

Radiation therapy is a cancer treatment using beams of intense energy (such as X-rays, protons, or others) in order to kill cancer cells. Radiation can be applied from a machine outside the body that targets the beams to a precise point where a tumor is located. Alternatively, radiation can be applied from inside the body with brachytherapy. Radiation therapy can be used as a primary treatment, before surgery, after surgery, or in combination with other cancer treatments.

During the treatment planning process, CT or other types of scans are used to determine the exact location of the tumor. While the target of radiation therapy is cancerous cells, healthy cells are also generally affected in the area of the tumor.

Therefore, there remains a need for an effective method of managing multiple drugs and suggesting appropriate doses based on the combination of drugs being taken. There also remains a need for dosing cancer therapies while minimizing damage to healthy cells.

SUMMARY OF THE INVENTION

The present invention provides for a method of dosing cancer therapies, by collecting patient data including cancer therapies/drugs to be taken, analyzing the data in view of dosing criteria established based on outside data, and determining a dose for each cancer therapy/drug taken.

The present invention further provides for a logic engine for dosing cancer therapies, including an algorithm stored on non-transitory computer readable media for collecting clinical trial data to establish criteria for dosing cancer therapies/drugs to a single patient and patient data and storing the clinical trial data and patient data in a database, analyzing the patient data in view of criteria established from the clinical trial data, and determining a dose for each cancer therapy/drug.

The present invention generally provides for a method of adjusting treatment of a cancer patient, by a patient inputting data about nutrition, medication, lifestyle, symptoms, and user defined metrics in an application, integrating data from outside devices and outside databases including updated patient scans, performing an analysis on the data, outputting a result from the data to medical professionals, and the medical professionals adjusting the treatment of the patient based on the data.

DESCRIPTION OF THE DRAWINGS

Other advantages of the present invention are readily appreciated as the same becomes better understood by reference to the following detailed description when considered in connection with the accompanying drawings wherein.

DETAILED DESCRIPTION OF THE INVENTION

Figure 1:
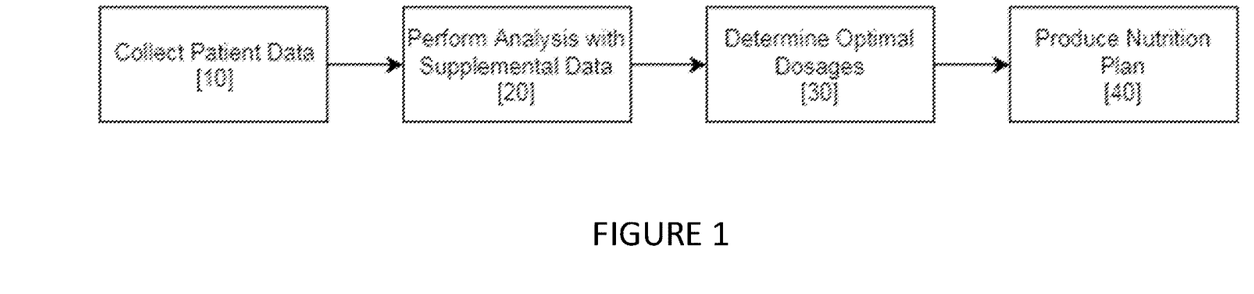
FIG. 1 is a schematic of the method of the present invention.

The present invention generally provides for methods of safely and efficaciously dosing cancer therapies, especially multiple cancer therapies taken together along with other drugs and especially in view of patient scans, to ensure that patients receive a safe and effective dose of each drug. Most generally, as shown in FIG. 1, the method includes collecting patient data 10 with treatment plan details including cancer therapies to be taken, analyzing the data in view of outside data 20, and determining a dose for each cancer therapy with output data 30. The dose determination is an optimization of maximizing therapeutic effect while minimizing likelihood of adverse effects for the combination of cancer therapies taken. This will consider data relating to pharmacokinetics, distribution, prior toxicity and efficacy determinations, age, metabolism, any other criteria related to toxicity and efficacy outcomes, as well as tumor scans. In other words, known data is compiled from prior clinical data studies (Phase 1 through Phase 4 trials) and compared to specific patient data in order to predict proper safe and efficacious dosing of cancer therapies. The analysis of data provides an understanding of complex drug-drug interactions not presently accounted for which can alter toxicity and efficacy of each individual drug. The goal is to provide the combination of drugs while ensuring dosing of each is safe and efficacious in spite of the drug-drug interactions. The method can further include dispensing the cancer therapies to the patient in the prescribed dose 40. In the case of dispensing, the present invention ensures sufficient evaluation criteria was provided before suggesting an outcome. The present invention further provides for a logic engine (i.e. a computer program) for performing the method, including an algorithm stored on non-transitory computer readable media for collecting patient data 10 and storing the patient data in a database 50, analyzing the patient data in view of outside data 20, and determining a safe and efficacious dose for each drug with output data 30. The logic engine performs the complex analysis of data input for each drug in the regimen, accounts for all drug-drug interactions, and determines safe and efficacious dosing. This analysis becomes quite complex when there are greater than two drugs being administered, which is quite common in cancer therapeutics.

"Cancer therapy" as used herein, refers to any treatment for cancer, including, but not limited to, radiation, surgery, chemotherapy, or other drugs such as for pain management or nausea. The present invention is especially useful in dosing combinations of cancer therapies, as well as with other general drugs, nutritional supplements, and vitamins.

The cancer therapy can include, but is not limited to, abiraterone acetate, methotrexate, paclitaxel albumin-stabilized nanoparticle formulation, ABVC (doxorubicin hydrochloride, bleomycin, vinblastine sulfate, dacarbazine combination), ABVE (doxorubicin hydrochloride, bleomycin, vinblastine sulfate, etoposide combination), ABVE-PC (doxorubicin hydrochloride, bleomycin, vinblastine sulfate, etoposide, prednisone, cyclophosphamide combination), AC (doxorubicin hydrochloride and cyclophosphamide combination), AC-T (doxorubicin hydrochloride, cyclophosphamide, paclitaxel combination), brentuximab vedotin, ADE (cytarabine, daunorubicin hydrochloride, etoposide combination), ado-trastuzumab emtansine, doxorubicin hydrochloride, fluorouracil, afatinib dimaleate, everolimus, imiquimod, aldesleukin, alemtuzumab, pemetrexed disodium, palonosetron hydrochloride, chlorambucil, aminolevulinic acid, anastrozole, aprepitant, pamidronate disodium, exemestane, nelarabine, arsenic trioxide, ofatumumab, asparaginase *Erwinia chrysanthemi*, bevacizumab, axitinib, azacitidine, BEACOPP (bleomycin, etoposide, doxorubicin hydrochloride, cyclophosphamide, vincristine sulfate, procarbazine hydrochloride, prednisone combination), carmustine, belinostat, bendamustine hydrochloride, BEP (bleomycin, etoposide, cisplatin combination), bevacizumab, bexarotene, tositumomab, I 131 Iodine tositumomab, bicalutamide, carmustine, bleomycin, bortezomib, bosutinib, busulfan, cabazitaxel, cabozantinib-S-malate, CAF (cyclophosphamide, doxorubicin hydrochloride, fluorouracil combination), irinotecan hydrochloride, capecitabine, CAPDX (capecitabine, oxaliplatin combination), carboplatin, carboplatin-taxol combination, carfilzomib, carmustine implant, lomustine, ceritinib, daunorubicin hydrochloride, recombinant HPV bivalent vaccine, cetuximab, chlorambucil, chlorambucil-prednisone combination, CHOP (cyclophosphamide, doxorubicin hydrochloride, vincristine sulfate, prednisone combination), cisplatin, cyclophosphamide, clofarabine, CMF (cyclophosphamide, methotrexate, fluorouracil combination), COPP (cyclophosphamide, vincristine sulfate, procarbazine hydrochloride, prednisone combination), COPP-ABV (cyclophosphamide, vincristine sulfate, procarbazine hydrochloride, prednisone, doxorubicin hydrochloride, bleomycin, vinblastine sulfate combination), dactinomycin, crizotinib, CVP (cyclophosphamide, vincristine sulfate, prednisone combination), ifosfamide, ramucirumab, cytarabine, liposomal cytarabine, dabrafenib, dacarbazine, decitabine, dactinomycin, dasatinib, degarelix, denileukin diftitox, denosumab, dexrazoxane hydrochloride, docetaxel, doxorubicin hydrochloride liposome, fluorouracil, rasburicase, epirubicin hydrochloride, oxaliplatin, eltrombopag olamine, enzalutamide, EPOCH (etoposide, prednisone, vincristine sulfate, cyclophosphamide, doxorubicin hydrochloride combination), eribulin mesylate, vismodegib, erlotinib hydrochloride, etoposide phosphate, etoposide, everolimus, raloxifene hydrochloride, toremifene, fulvestrant, FEC (fluorouracil, epirubicin hydrochloride, cyclophosphamide combination), letrozole, filgrastim, fludarabine phosphate, fluorouracil, FOLFIRI (leucovorin calcium, fluorouracil, irinotecan hydrochloride combination), FOLFIRI-bevacizumab combination, FOLFIRI-cetuximab combination, FOLFIRINOX (leucovorin calcium, fluorouracil, irinotecan hydrochloride, oxaliplatin combination), FOLFOX (leucovorin calcium, fluorouracil, oxaliplatin combination), pralatrexate, FU-LV (fluorouracil, leucovorin calcium combination), recombinant HPV quadrivalent vaccine, obinutuzumab, gefitinib, gemcitabine hydrochloride, gemcitabine-cisplatin combination, gemcitabine-oxaliplatin combination, gemtuzumab ozogamicin, imatinib mesylate, glucarpidase, goserelin acetate, trastuzumab, topotecan hydrochloride, hyper-CVAD (cyclophosphamide, vincristine sulfate, doxorubicin hydrochloride, dexamethasone combination), ibritumomab tiuxetan, ibrutinib, ICE (ifosfamide, carboplatin, etoposide combination), ponatinib hydrochloride, idarubicin hydrochloride, idelalisib, ifosamide, axitinib, recombinant interferon α-2b, ipilimumab, irinotecan hydrochloride, romidepsin, ixabepilone, ruxolitinib phosphate, palifermin, pembrolizumab, lapatinib ditosylate, lenalidomide, letrozole, leucovorin calcium, leuprolide acetate, vincristine sulfate liposome, procarbazine hydrochloride, mechlorethamine hydrochloride, megestrol acetate, trametinib, mercaptopurine, mesna, temozolomide, mitomycin C, mitoxantrone hydrochloride, MOPP (mechlorethamine hydrochloride, vincristine sulfate, procarbazine hydrochloride, prednisone combination), plerixafor, vinorelbine tartrate, nelarabine, sorafenib tosylate, nilotinib, tamoxifen citrate, romiplostim, obinutuzumab, ofatumumab, omacetaxine mepesuccinate, pegaspargase, OEPA (vincristine sulfate, etoposide, prednisone, doxorubicin hydrochloride combination), OFF (oxaliplatin, fluorouracil, leucovorin calcium combination), OPPA (vincristine sulfate, procarbazine hydrochloride, prednisone, doxorubicin hydrochloride combination), paclitaxel, PAD (bortezomib, doxorubicin hydrochloride, dexamethasone combination), palifermin, palonosetron hydrochloride, pamidronate disodium, panitumumab, pazopanib hydrochloride, peginterferon α-2b, pembrolizumab, pemetrexed disodium, pertuzumab, plerixafor, pomalidomide, ponatinib hydrochloride, pralatrexate, prednisone, procarbazine hydrochloride, sipuleucel-T, radium 223 dichloride, R-CHOP (rituximab, cyclophosphamide, doxorubicin hydrochloride, vincristine sulfate, prednisone combination), R-CVP (rituximab, cyclophosphamide, vincristine sulfate, prednisone combination), reforafenib, rituximab, romidepsin, ruxolitinib phosphate, talc, siltuximab, sipuleucel-T, sorafenib tosylate, STANFORD V (mechlorethamine hydrochloride, doxorubicin hydrochloride, vinblastine sulfate, vincristine sulfate, bleomycin, etoposide, prednisone combination), sunitinib malate, thalidomide, TAC (docetaxel, doxorubicin hydrochloride, cyclophosphamide combination), temozolomide, temsirolimus, topotecan hydrochloride, toremifene, TPF (docetaxel, cisplatin, fluorouracil combination), trametinib, trastuzumab, vandetanib, VAMP (vincristine sulfate, doxorubicin hydrochloride, methotrexate, prednisone combination), VeIP (vinblastine sulfate, ifosamide, cisplatin combination), vinblastine sulfate, vemurafenib, vincristine sulfate, vincristine sulfate liposome, vinorelbine tartrate, VIP (etoposide, ifosfamide, cisplatin combination), vismodegib, vorinostat, XELOX (capecitabine, oxaliplatin combination), ziv-aflibercept, zoledronic acid, or combinations thereof.

The cancer therapy can also include site specific immunomodulators (SSIs) that provide a targeted immune response in particular organs such as, but not limited to, QBECO (targeting the colon), QBKPN (targeting the lung), QBSAU (targeting skin, breast, and bones), or QBECP (targeting the prostate and urinary tract) (Qu Biologics).

Most generally, the flow of information used in the present invention is Data Input→Central AI↔Healthcare Professional. The data input can be from, but is not limited to, clinics, electronic medical records (EMRs), pharmaceutical companies, private databases, or CROs. The healthcare professional can be, but is not limited to, an MD, pharmacist, hospital, insurer, nurse, laboratory professional, or other medical professional. The healthcare professional can then input data regarding the patient back into the central AI such as, but not limited to, patient data from monitors (including at a medical facility and personal monitors such as smart devices), data from EMRs, physical exams, or insurance information. Data inputs collected and received can include real time data streams from devices including but not limited to cardiovascular monitors and wearable smart devices.

After passing input data to the central AI, the AI extracts all features relating any and all variables that effect drug metabolism. Feature extraction includes elements relating how these variables are affected by dosing of additional consumed drugs.

The AI applies a predeveloped feature-rich model to a patient's specific physiology, metabolism, etc. for cancer therapies and drugs being taken. As these features can be induced to change by a change in disease state, drug induced changes, etc., real time monitoring of these changes can assist in real time drug dosing adjustments. While such a system may not be practical for all home care, it is practical for patients already on monitors and mechanically/digitally receiving drugs and further enabled by the increased use of wearable diagnostic devices.

The system is cancer therapy/drug centric. The AI creates a model relating dosing to patient condition and effect of other cancer therapies/drugs on that condition which effect efficacy of all cancer therapies/drugs taken and toxicity of all cancer therapies/drugs taken. The AI can generate subsets of features to handle complicated multivariable relationships with simple output of recommended dosing range of the multiple cancer therapies/drugs, or actually in real time administer those cancer therapies/drugs. The general factors/variables in the model can be, but are not limited to, age of patient, weight of patient, known side effects of cancer therapies/drugs alone and in combinations with other cancer therapies/drugs, known toxicity range as related to ED 50 and other dose response points of interest, efficacy ranges, and chronic treatment effect versus acute treatment (one time dosing versus dosing over time). Such factors can be gathered from clinical studies along with other information as necessary and then the patient can be fit into model to determine dosing for cancer therapies/drugs needed. Added to the above can be a remote patient monitoring platform to provide input regarding the progress or failure of the therapy. Based on this information, the present algorithm can adjust the dosing accordingly, be more aggressive, or suggest substitute drug combinations.

Figure 2:
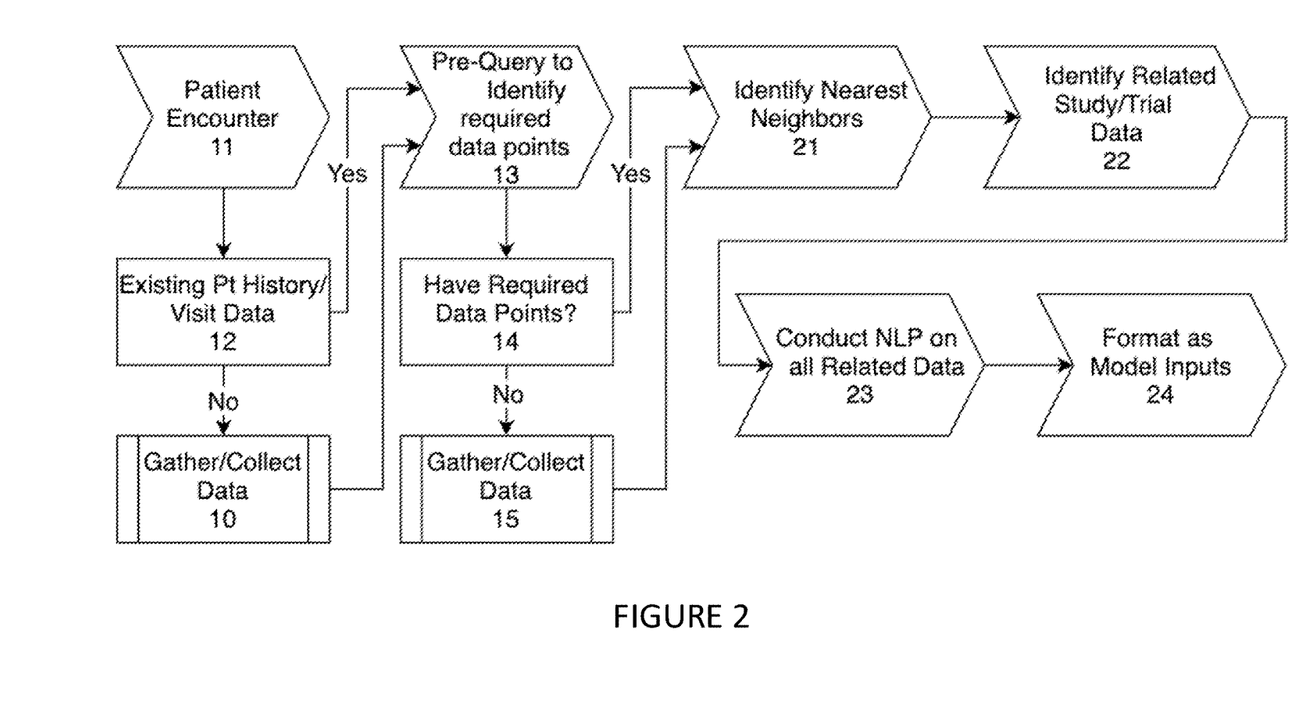
FIG. 2 is a schematic of the method of the present invention.
Figure 4:
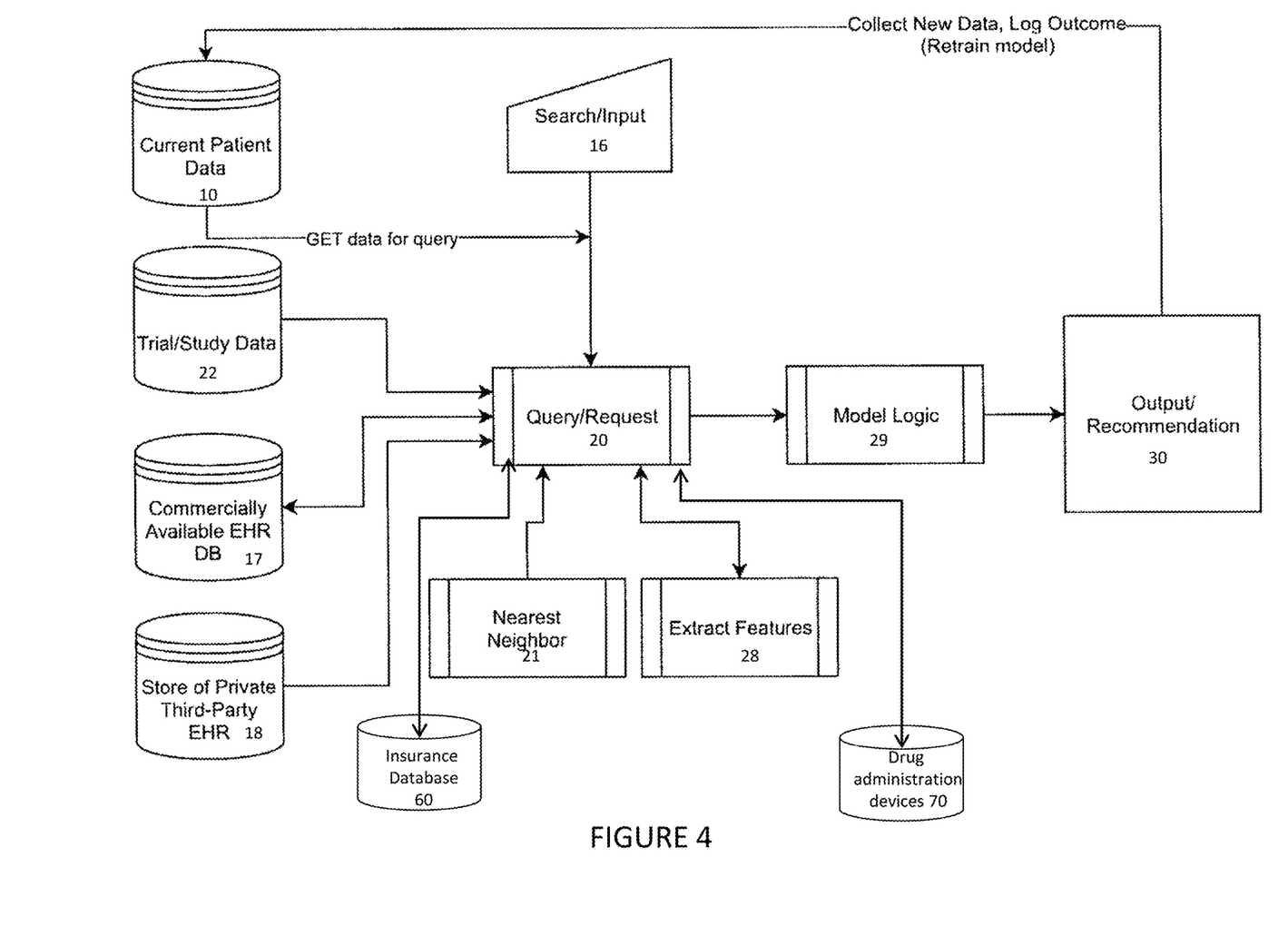
FIG. 4 is a schematic of the method of the present invention.

The method and logic engine are shown in greater detail in FIGS. 2 and 4. At a patient encounter 11, it is first determined if there is any existing fit history or visit data 12. If not, patient data can be collected 10 as detailed below. A pre-query 13 is performed to identify any required data points to perform an analysis. If the required data points 14 are not present, then they are gathered or collected 15. Next, the nearest neighbors are identified 21, related study/trial data is identified 22, Natural Language Processing (NLP) is conducted on related unstructured data 23, before being conditioned as program inputs 24. Natural Language Processing is a type of AI that extracts features from unstructured text, such as, but not limited to, patient notes or items appearing in 'other' categories in drug trials. The unstructured data can also list additional side effects, or notes from any informal exams.

Various data is collected about the patient 10 and entered into a database 50 on computer readable media. This includes symptoms, diagnoses, and proposed cancer therapies/drugs/treatments 16 that the patient has been prescribed to take by a doctor or other medical professional. More specific data can be collected from analysis of blood and urine samples related infectious disease, metabolism, presence of antigen indicated disease (such as cancer, MS, etc.), patient temperature, blood pressure and other data routinely or additionally collected by the health care professional or present in the patient's electronic health record.

Fixed demographics can be collected, such as, but not limited to, age, gender, race, height, known drug interactions, and body composition (fat, muscle content). All of these criteria, including genetic inclination to drug metabolism and general metabolism, resistance and susceptibility to disease, and other related criteria are analyzed, as each can be individually pertinent related to the metabolism of each individual cancer therapy/drug prescribed and taken by the patient, as well as the combined effects of each of the cancer therapies/drugs on each other. In other words, consideration is taken into account regarding the cancer therapies/drugs individual effects on the patient as well as the effects of the combined combination of cancer therapies/drugs being taken.

Temporal values can be collected, such as, but not limited to, historic values from existing electronic medical records (EMR) or electronic health records (EHR), current/up to date values, cholesterol, blood pressure, weight, and diagnostics related to a specific ongoing disease. The database 50 can be in electrical connection with commercially available EHR databases 17 and private third-party EHR databases 18 to search for relevant data and extract data to the database 50 for analysis. Patient data related to diet (i.e. specific foods eaten often, especially ones known to have interactions with cancer therapies/drugs) and nutritional supplements can also be collected, as well as exercise habits.

Genetic components can be collected, such as, but not limited to, key genetic markers, whole genome data from genetic testing/ancestry sites, or test results from any type of genetic tests. Genetic components are important not just for markers for known drug efficacy, but also for generating ethnicity and demographics features for multidimensional nearest neighbor calculations (further described below). The known effects of drugs on liver enzymes, critical to first pass drug metabolism will be considered and analyzed as each drug alone and in combination effects the liver enzymes differently. So the capacity of the patient's liver enzymes as well as the drug effect on the liver enzymes are synthesized in the analysis. Genetic testing results can be obtained from databases in companies such as 23andMe, AncestryDNA, Living DNA, HomeDNA, National Geographic Genographic Project, or MyHeritageDNA. With genetic tests, a patient's cheek can be swabbed or scraped, or spit can be collected to analyze the DNA in order to determine if cancer or viruses are present. Other genetic tests can be performed to collect additional information regarding viruses and cancer within the body that may not be obtainable from a swab or spit from samples such as, but not limited to, blood, plasma, urine, other fluids, or tissue samples from biopsies.

Various imaging can be collected, such as, but not limited to, CAT scans, CT scans, X-rays, MRI, ultrasounds, PET scans, or other visual analyses especially of tumors. Reports from imaging studies are analyzed and encoded using an NLP algorithm to extract features. These features, along with structured findings from a radiologist are used to inform the model.

Unstructured data can also be collected, such as, but not limited to, any patient notes over time. Natural language can be processed into a network of classifiers to identify propensities for certain risk factors, given certain patient notes. For example, there may be a correlation between the presence of hygiene concerns in a patient note and reduced likelihood of adherence to a drug therapy regime. Unstructured patient data includes notes by healthcare professionals as well as information collected directly from the patient including responses questionnaires, intake forms, etc.

This patient data structure, when fully populated, contains the full digital footprint needed to make queries into the logic engine. Instead of a fixed patient data structure, the patient model is fluid and its makeup of fields is determined by the desired outcome of the model. This reflects the fluidity of the patient's stasis as the patient's condition ultimately requiring the need for cancer therapies/multiple drug consumption and the related dosing is fluid as the patient initially succumbs to a disease, is treated with the cancer therapies/drugs, further scans of the tumors are analyzed, and then hopefully recovers from the disease. As the patient's stasis changes and hopefully returns to homeostasis, dosing can be altered, especially based on updated patient scans.

The logic engine can request supplemental data 13 based on the patient data. Once trained, the logic engine has the ability to apply a discrete weighting regime to extracted features 28 based on their significance, i.e. request a blood level or demographic data point prior to making a dosing recommendation, imaging, pharmacogenomics testing, lifestyle questions, or any other type of diagnostics required. Different intended drug combinations will require different sets of supplemental data. Additional data selection can be weighted by importance, invasiveness, cost, and availability. For example, if a certain test is not available or prohibitively invasive, the logic engine reacts accordingly by being transparent with the decreased accuracy or exposure to potential risk.

Since the required input data varies on numerous conditions, essential data points are unknown until the basic query has started. If no further data is needed, the logic of the present invention can continue without additional input. Also, data can be weighted and combinations of data can be weighted.

Figure 5:
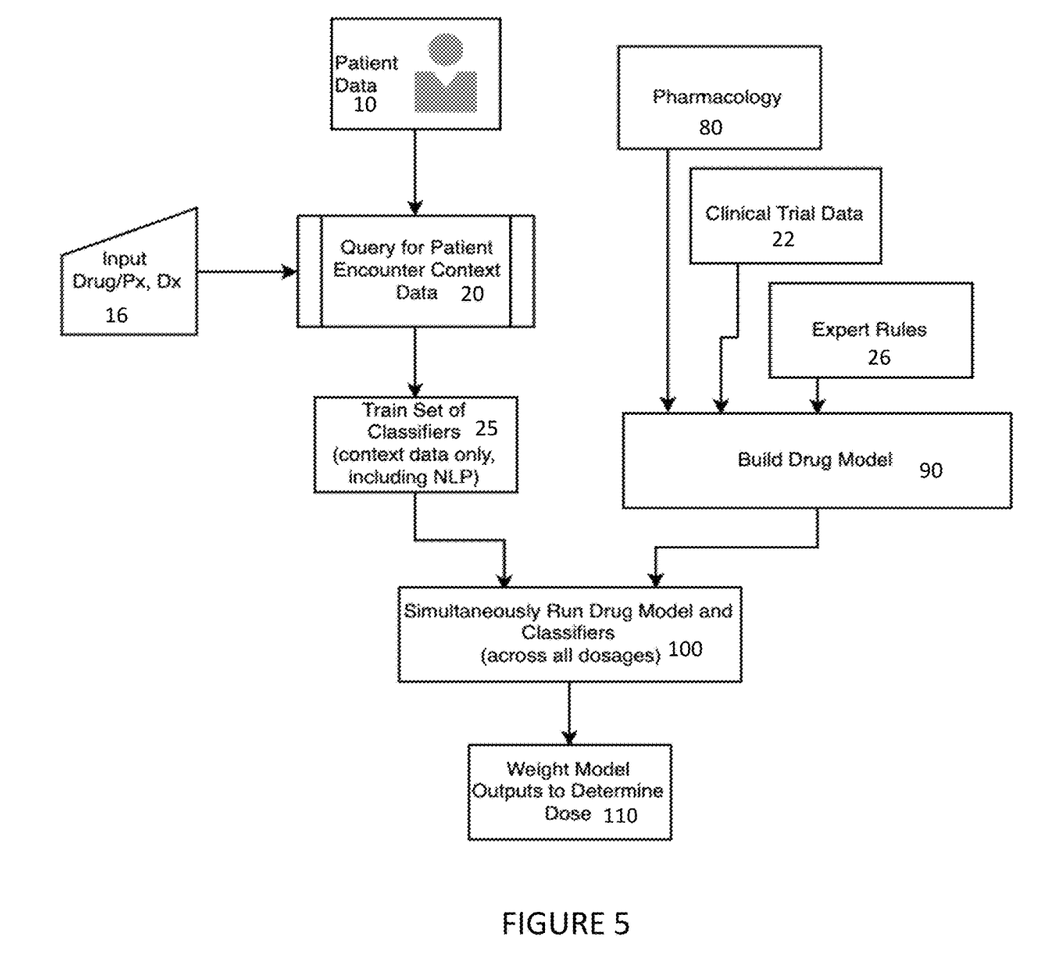
FIG. 5 is a schematic of the method of the present invention.

The database 50 can also collect information relating to the cancer therapies/drugs desired to be prescribed (i.e. pharmacology information 80, shown in FIG. 5). Pharmacology information 80 can include drug mechanism of action, the safe dosage range, the suggested dosing strategy, and other pharmacological properties such as liberation, absorption, distribution, metabolism, and excretion. These factors and any other available information are taken into consideration to develop the drug-based model.

Prescriptions of certain drugs (or combinations of drugs) can require pharmacogenomic testing to check for certain markers. These markers can help decide between different classes of drug, circumvent known risk factors, as well as optimize the dosages. Since the effectiveness of a therapy is influence by the presence of certain markers, the results from genetic testing can be critical inputs. Pharmacogenomic testing is widely used when evaluating medications used in the treatment of ADD/ADHD and depression, anticoagulants, and others. The use and availability of data from pharmacogenomic testing is on the rise due to decreasing costs.

Mimicking the human expert decision making process, all data pertinent to making an informed decision must be made available and formatted prior to running the logic engine. The logic engine can proceed with missing data points, however, accuracy and therefore confidence in the decision are reduced.

Nearest neighbor data can be identified 21. A key aspect to the success of the present invention is the use of data from similar patient data markers. A "nearest neighbor", as used herein, can be persons that have similar patient data and/or underwent a treatment plan with similar cancer therapies or drug combinations. Identifying existing records similar to the patient in treatment is a key component to the accuracy of the logic engine. A multi-dimensional nearest neighbor algorithm is used to find those individuals from existing sets, i.e. a K-Nearest Neighbor (KNN) algorithm. The KNN algorithm is a clustering algorithm and acts as a non-parametric untrained classifier that evaluates the overall similarity between two patients/subjects based on the degree of differences across multiple features. The flexibility of such an algorithm allows consideration of many parameters when searching for pertinent context data. Weights on certain factors can vary depending on the type of diagnosis and class of drug. For example, a patient might be more willing to risk side effects in exchange for efficacy. These similar patient profiles are grouped into subsets to look for trends that can be used to optimize the treatment plan of the given patient. While the KNN algorithm can be preferred, other clustering algorithms can also be used, such as, but not limited to, K-Means, Affinity Propagation, Mean Shift, Spectral Clustering, Support Vector Machines. One advantage of KNN over other techniques is that it is easily scalable across many dimensions. Further, from case-to-case the differing dimensions and weights are easily included. Nearest neighbors can also be identified from genetic testing databases who have also been treated for similar diseases or with similar treatments, or from patients who have similar scans.

The purpose of the KNN algorithm is to find patients most similar to the present patient. Once identified, the "neighboring" patient data, including treatment plan and outcome, are used to evaluate the present subject. To make the identification, the differences in each parameter comprising the patient data structure are evaluated. While most commonly used with continuous values (weight, age, LDL level, etc.), the algorithm can be used with discrete values as well (race/ethnicity, familial history, presence of certain symptoms, etc.). The differences across each parameter are combined using a weighting scheme such that a normalized 'distance' is produced representing an overall difference metric between two patients. The distance calculation between two patients is achieved using a regression-type KNN algorithm. Key to the regression evaluations is the Mahalanobis distance. The Mahalanobis distance evaluates to a Euclidian distance since the covariance matrix is always the identity matrix, i.e., one parameter in this case is never to be compared independently with another parameter. The benefit of adapting the Mahalanobis distance instead of using pure Euclidian distance is that Mahalanobis distance includes the measurement of the number of deviations away from the norm. While the actual standard deviation is not always ideal, an equivalent term is used.

If the present patient $P_1$ has a set of parameters where $P_1 = \{\mu_{1P1}, \mu_{2P1}, \mu_{3P1}, \ldots \mu_{NP1}\}$ and an arbitrary patient, $P_\beta$, where $P_\beta = \{\mu_{1P\beta}, \mu_{2P\beta}, \mu_{3P\beta}, \ldots \mu_{NP\beta}\}$, then the distance, D, between the two patients is:

$$D_1(P_1, P_\beta) = \sqrt{\Sigma_{i=1}^N (\mu_{iP1} - \mu_{iP\beta})^2}$$

Several adaptations are needed to the above generalized equation. Mainly, handling a weighting schema. Most simply, a set of weights, W, should be created with each parameter in P being assigned a weight. Weights can be applied using any technique. Shown below is an intuitive 1-10 linear weighting schema. If $W = \{\rho_1, \rho_2, \rho_3, \ldots \rho_N\}$, then the distance, D, can be evaluated by:

$$D_1(P_1, P_\beta) = \sqrt{\Sigma_{i=1}^N \rho_i (\mu_{iP1} - \mu_{iP\beta})^2}$$

In the above examples for $D_1$ and $D_2$ continuous values are used for $\mu_N$. In this application, continuous values can be integers or rational numbers. Discrete values must be handled in a special manner. Since there is no intuitive value for the difference between two ethnicities, one must be manually supplied in a lookup table. Algorithmically, parameters with continuous values should be summated using the squared difference while parameters with continuous values are summated manually. The same $W = \{\rho_1, \rho_2, \rho_3, \ldots \rho_N\}$ weighting schema applies to discrete parameters as well.

The threshold for evaluating whether or not another patient is sufficiently similar to the present patient is situational. The ideal number of similar subjects is to be optimized on a case-to-case basis when there exists sufficient training data.

KNN algorithms have been used before. For example, U.S. Pat. No. 10,123,748 (IBM) discloses a Patient Risk Analysis method that uses KNN to find similar patients. U.S. Pat. No. 7,730,063 discloses a personalized medicine method that also mentions KNN as a potential algorithm for finding similar patients. The present invention's ability to include continuous and discrete parameters as well as customized weights in the KNN differentiates over these prior art methods.

The inputs to the logic engine are broad and complex. AI techniques such as the KNN algorithm are applied to the inputs to precondition the data. By taking this step to precondition data, the following processing steps are simplified.

The logic engine employs a combination of artificial intelligence techniques, both supervised and unsupervised. Instead of using a broad-scale program that is trained once, the logic engine in the present invention is unique to the inputs and is therefore trained on demand. The benefit to this technique is to emphasize the individuality of the patient and the symptoms.

Figure 3:
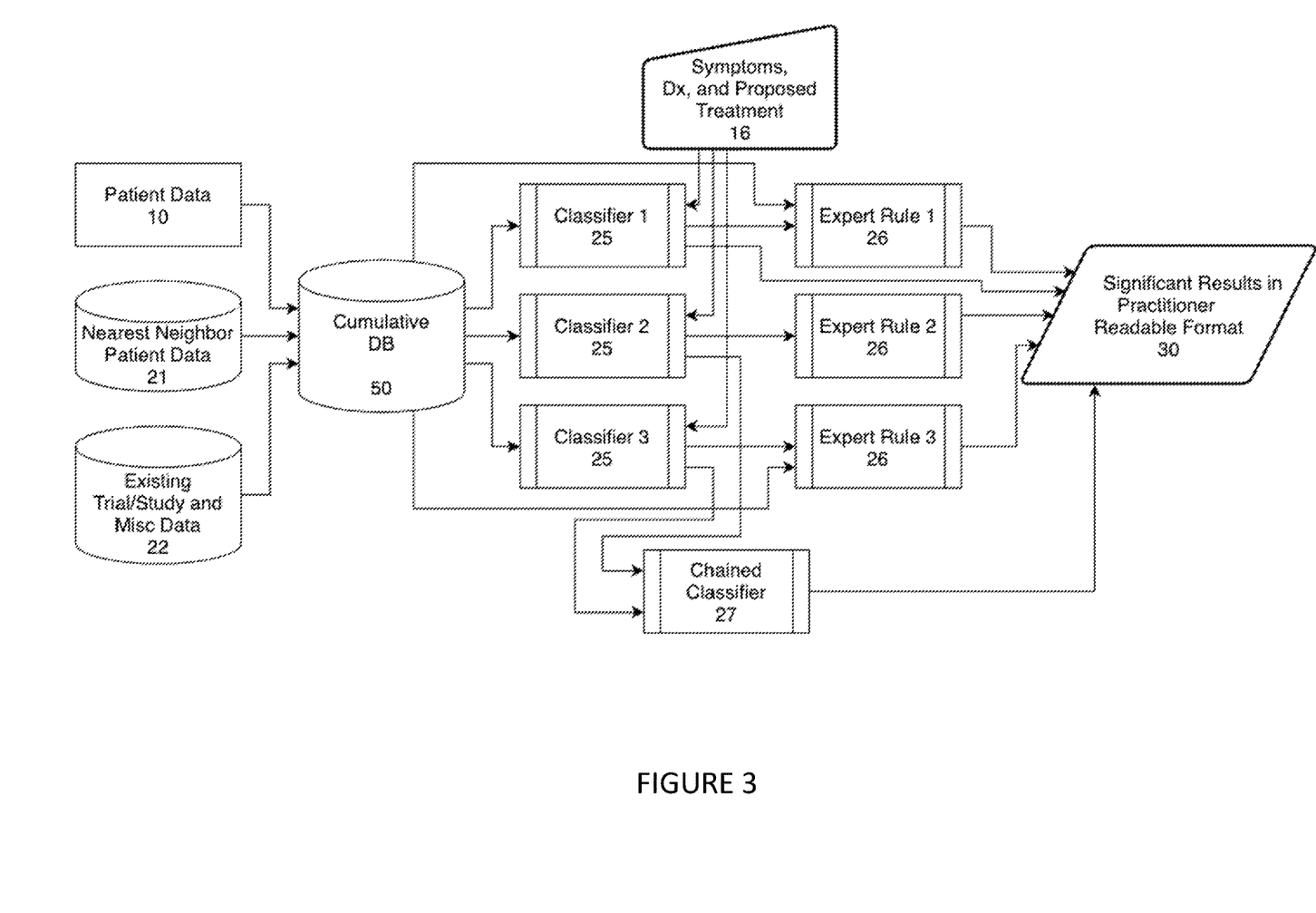
FIG. 3 is a schematic of classifiers and expert rules in the method.

Most broadly, and as shown in FIG. 3, the present invention includes model logic 29 composed of a series of classifiers 25, some of which offer direct outputs (such as the likelihood for an occurrence of a direct drug interaction or the presence of a certain side effect), while others perform intermediary steps. Classifiers 25 and expert rules 26 implemented in series is a strategy known as chaining 27, a process that takes advantage of the smaller preprocessing steps conducted by earlier-staged processing. Processing data using classifiers 25 in this way codes the patient information into a format suitable for use in existing artificial intelligence techniques. Most commonly, this involves assigning a quantitative element to inherently non-quantitative data. Data points, such as the presence of a side effect, are turned into features. Data elements can be Boolean or continuous depending on the type. Each individual data element is assigned a confidence and a weight. The confidence is a representation of the accuracy of the element, while the weight represents the importance.

The expert system also contains a series of rules 26 prepopulated by practitioners. These rules 26 can be drug or drug-class specific and compose the supervised learning aspect of the AI. In the spirit of fuzzy logic systems, each rule 26 is assigned a varying degree of truth, establishing a crude weighting scheme.

The classifiers 25 and the drug model 90 are ran simultaneously across all possible dosage ranges 100. For each dosage, classifications with confidence intervals are calculated. The generic drug model is ran using the same set of dosages mapped out to the same classifiers used when evaluating context data. The outputs from both models are weighted and combined to determine the optimal dose 110 in the output 30.

A major differentiator with the present invention relates to the mimicked expert output 30 of the logic engine. The output of the logic engine is an overall comprehensive analysis of the present patient, the diagnosis, and the primary method of treatment with dosages for each diagnosis. Any notable findings related to drug interaction, decreased efficacy, or side effect management are incorporated into the output. In this way, the full treatment plan is considered rather than the industry status quo of evaluating the possibility of toxicity or otherwise adverse reaction. It accomplishes producing an output based on data not accessible by the practitioner or pharmacist. Analysis is provided to determine output presently not considered by the practitioner. Presently, the only assistance to the practitioner or pharmacist is in the nature of do or do not do. That is, do give certain drugs together or do not based on general know toxicities. Nothing is available that assists in not only minimizing toxicity, but also maximizing efficacy of drug combinations. Furthermore, with respect to cancer therapies, the output 30 takes into account the updated scans of the patient to minimize damage to healthy tissue by updating dosing, especially when providing radiation therapy.

The format of the output 30 can be a practitioner readable report with information being displayed in a manner to easily allow the user to identify categories of alerts. Certain outputs 30 can alter the course of a treatment altogether while other times an output might reinforce a direction in an attempt to mitigate an already known side effect. When applicable, the likelihood or confidence approximation is presented as well. This transparent output 30 format is all in an attempt to synthesize relative information when the practitioner is facing a treatment decision.

The output 30 can also be sent to a pharmacy or self-dispensing machine where the determined dose of each drug can be prepared for the patient 40. The output 30 can also provide the patient with instructions of how to take each drug and side effects to watch out for, as well as contraindications with commonly taken over the counter medications, supplements, and food. The output 30 can be sent wirelessly to any medical professional or the patient to read on a mobile device, tablet, laptop, or desktop computer. While doctors can use the logic engine to initially prescribe drugs at a certain dose to a patient, the logic engine can also be used by pharmacists to check a doctor's prescription in view of the other drugs that the patient is currently taking to make sure that the dose is correct and to reduce side effects.

The database 50 can further be in electronic communication with an insurance company's databases 60 and have access to a particular patient's insurance plan. Once a particular dose of the cancer therapy/drug combination has been determined, the logic engine can further analyze the feasibility of the patient taking the particular combination of cancer therapies/drugs according to what their insurance will cover. The logic engine can determine costs for the patient and determine if a generic drug is available for a particular input drug, or if a similar working drug that costs less is available. If a similar lower-cost drug is available, the logic engine can provide optimal dosing for that drug as a substitute as well as any information regarding side effects or efficacy as compared to the original input drug.

The database 50 can also be in electronic communication with drug administration devices 70. This can be to the extent of real time dosing, administration, patient data gathering, and dosing adjustment based on the real time data. In other words, after running the logic engine, and based on the recommended doses of drugs taken by the patient, the drug administration device 70 can receive updated dose information and adjust future doses accordingly. Electronic communication can be wireless or wired (such as with BLUETOOTH® or downloadable with a USB connection) and signals can be sent at the time that a dose is administered. These devices can include, but are not limited to, transdermal patches, intravenous drips, self-injection and auto-injection devices, wearable injection devices, and implantable drug delivery devices.

The database 50 can also be in electronic communication with a user friendly application 200 that can capture daily activities, intake, and symptoms of patients that can be useful to determine hidden patterns and effects as well as monitor the effects of the cancer therapies and/or other drugs in order to make adjustments in dosing or suggest alternative treatments to medical professionals. It should be understood that the application 200 can be used for monitoring the treatment of any drug that the patient is taking, such as for migraines. The information can be input by the user answering preset questions. Additionally, the information can be input from existing and newly developed outside monitoring devices. These monitoring devices can measure cardiac, circulatory or other physical properties of the user over time. The information gathered is analyzed over time along with patient gathered data gathered over time. This information enables users to tweak their lifestyle and feel better as well as after being sent to a medical professional, allows them to adjust their treatment plan as needed. The information can also be used to predict an adverse event happening at a later time point so that the user can either prevent the adverse event from happening with lifestyle changes or receive treatment to prevent the adverse event.

The term "application" as used herein refers to a computer software application, otherwise known as an "app", that is run and operated on a mobile device, such as, but not limited to, smart phones (IPHONE® (Apple, Inc.), ANDROID™ devices (Google, Inc.), WINDOWS® devices (Microsoft)), mp3 players (IPOD TOUCH® (Apple, Inc.)), or tablet computers (IPAD® (Apple, Inc.)), especially ones utilizing a touch screen. The application can also be web based and run on a computer or laptop. The application 10 includes any necessary user interface or display and storage components to display the application and store the algorithm running it.

"Trigger" as used herein, refers to an event or situation that causes or provokes a disease or condition to happen.

"Adverse event" as used herein, refers to any medical occurrence that is undesired in a user. Examples can include, but are not limited to, headaches, nausea, heart attacks, seizures, allergic reactions, hemorrhages, tissue damage, or any other damage to the body. Adverse events can cause disability, permanent damage, or even death.

Figure 6:
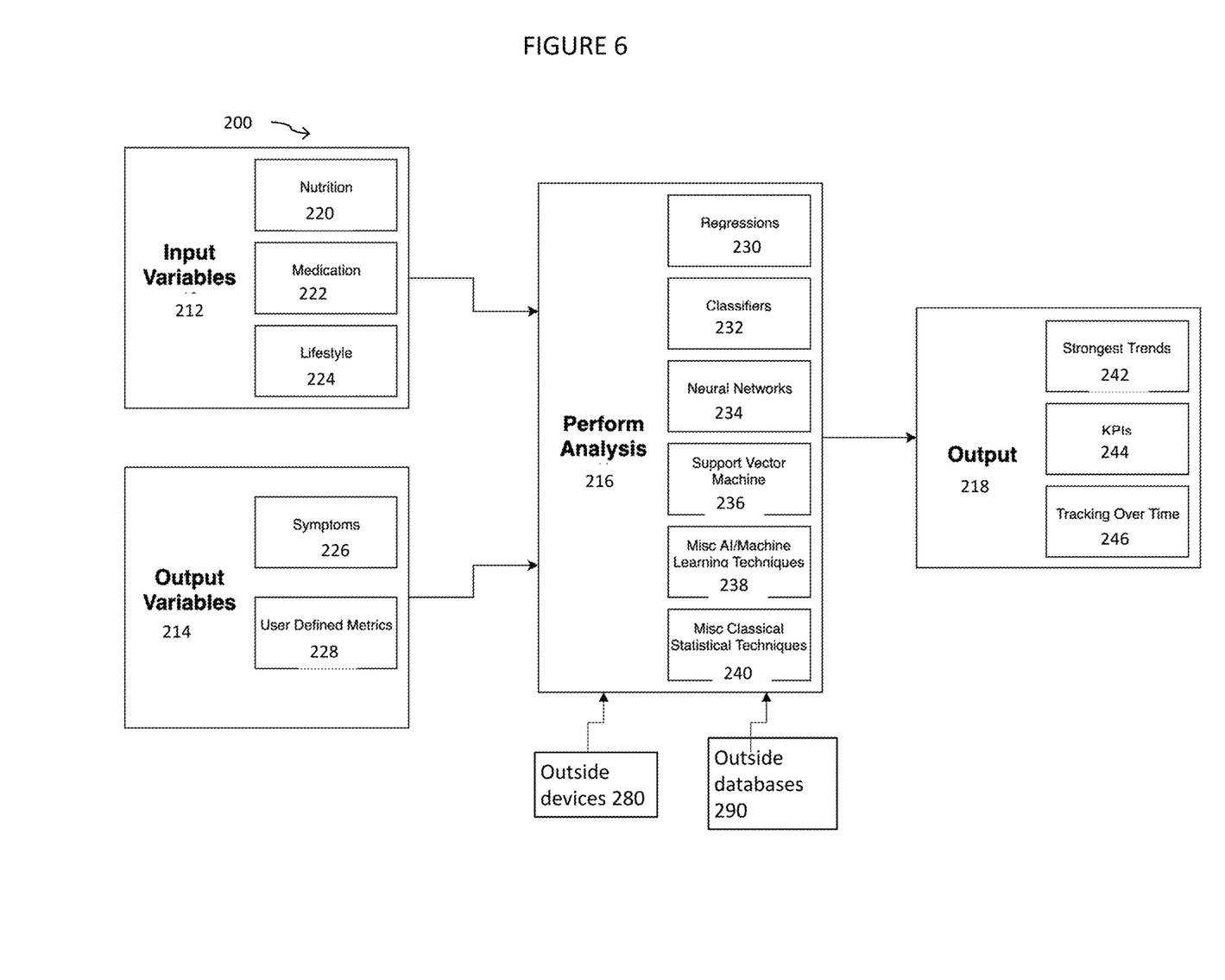
FIG. 6 is a diagram of the flow of information in the application and method.

As generally shown in FIG. 6, the application 200 includes an input module 212 for inputting variables from a user in electronic communication with an output variable module 214, an analysis module 216 that analyzes data from the input variables and output variables, and an output module 218 for presenting results to the user. Each of these modules can be run by algorithms stored on non-transitory computer readable media.

The input module 212 can be used to keep a daily log of users' lifestyle and symptoms. The questions are kept very simple so that a user can complete them in 1-2 minutes. The input module 212 can include a nutrition question module 220, a medication question module 222, and a lifestyle question module 224. Questions presented can be answered on a continuous or nominal scale. Input can also be gathered from various medical devices, such as portable monitoring systems, further described below. Accordingly, cardio, vascular, and neuro information can be input.

With the nutrition question module 220, questions can be presented to the user such as (with available answer choices in brackets):

How many servings of grains did you eat today? [0 to 10]
How many servings of fruit did you eat today? [0 to 5 or more]
How many servings of vegetables did you eat today? [0 to 5 or more]
How many servings of dairy did you eat today?
How much sugar did you have today? [0 to 5 scale, way less than average to way more than average]

With the medication question module 222, the user can input any medication they are taking, including vitamins and supplements, with dosing schedules and amounts.

With the lifestyle question module 224, questions can be presented to the user such as (with available answer choices in brackets):

How many hours of sleep did you get last night? [0 to 12+, on 0.5 intervals]
Did you workout today? [yes or no]
Did you take time to relax today [yes or no]
How stressed did you feel today? [0 to 5 scale]

The output variable module 214 can include a symptom question module 226 and a user defined metrics question module 228.

With the symptom question module 226, questions can be presented to the user such as (with available answer choices in brackets):

How much pain were you in today? [0 to 5 scale]
How many bowel movements did you have today? [0 to 10+, or on Bristol scale]
How many times did you pass blood? [0 to 10+]
Did you have a headache today? [yes or no]

The symptom question module 226 can also have questions as to whether a user is having a medical event, such as a migraine, asthma attack, or other medical event. The application 200 can also have a quick button that the user can easily access when a medical event is happening that can be clicked on or otherwise toggled. Such a quick button when used can automatically set up a reminder at a later time (such as several hours) to fully answer questions in the symptom question module 226 and/or medication question module 222.

With the user defined metrics question module 228, the user can design any other relevant questions and answers that could relate to their disease or condition that can be added to the application 10 to include in an analysis, such as alcohol intake or traveling.

All the data collected from the input module 212 and the output variable module 214 is sent to the analysis module 216. The analysis module 216 can include regressions 230, classifiers 232, neural networks 234, support vector machine 236, miscellaneous AI/machine learning techniques 238, and/or miscellaneous classical statistical techniques 240 in performing the analysis of the data.

In general, the analysis module 216 uses the data to find patterns between how users live and how they feel. By estimating multiple regressions 30 on time lagged variables, the application 200 can find patterns most people cannot casually notice or even calculate if they are keeping careful food diaries or medication diaries. With just one week of data, connections can be identified between how users live and how they feel.

The symptom variables can be used as the dependent variable in a series of regressions 230. The symptom variables include both same day, as entered values and time lagged, such that the first row of data is deleted out to four days later. The nutrition, medication, and lifestyle data measured are used as the independent, or predictor, variables. Linear regressions 230 are then estimated to determine which independent variables cause an increase in the symptoms, or dependent variables. The specific mechanisms are as follows. Users input their symptoms, food intake at a high level, medication intake, and simple lifestyle measures, each on a continuous or nominal (from Likert-type items) scales. The symptom variables include both same day, as entered values, and time lagged, such that the first row of data is deleted out to four days later. The food intake, medication, and lifestyle measured are used as the independent, or predictor, variables. Linear regressions are then estimated to determine which independent variables cause an increase in the symptoms, or dependent variables. Specifically, the symptom variables are then used as the dependent variables in a series of linear, ordinary least regressions. Within the first month of use, three regressions are estimated for each symptom. One regressions tests the food variables as the independent variables, one the lifestyle variables, and one the medication variables. Each regression coefficient with alpha <0.2 is flagged to users as a potential factor contributing to their symptoms. After users have inputted a full month of data, one master regression is estimated for each symptom outcome, combining the food, lifestyle, and medication predictor variables, thereby allowing the relative impact across categories to be determined. With the full month of data, the significance level drops to alpha <0.4.

Linear regressions 230 test the null hypothesis that the relationship between the independent variable(s) and dependent variable is 0. Unlike traditional data analysis, which requires a 5% alpha level to claim significance, the threshold for flagging potential lifestyle problems is lower. Specifically, the 5% standard level translates to a 95% likelihood that an effect is not due to chance, thereby rejecting the null hypothesis that the relationship is 0. But those who live with chronic illness want to know if there is a good chance, i.e., more than 60%, that a lifestyle choice, food, is causing symptoms. Further, the system can time lag outcome variables to capture the impact of day-to-day life on symptoms the same day, the next day, and the day after that. These regressions 230 serve as the steps in an algorithm.

While regressions 230 can be preferred, other methods of analysis can be used. Classifiers 232 are a broad use of artificial intelligence and machine learning that determine the relationship between input variables and output variables are categories. In the case of the present invention, it can be classified whether or not a specific user's data classifies as fitting the profile of effective lifestyle changes to help improve symptoms.

Neural Networks (NNs) 234 are another broad AI/machine learning technique that can be used to detect patterns in data. For the present invention, neural networks are one of the strategies used to identify trends in the data. NN models can be used for analyzing certain symptoms or broadly over the data set.

Support Vector Machines (SVMs) 236 can be used as part of the classification technique to identify certain features. SVMs rely on attempting regressions to evaluate which have the strongest fit with the data set.

Miscellaneous Machine Learning Techniques 238 can include other common AI techniques and combination of techniques.

Miscellaneous Classical Statistical Techniques 240 can include looking at distributions of data, means, deviations, tracking over time, etc. These techniques are commonly used as a part of feature extraction (to supplement the user-submitted data when running the models).

Nearest neighbor algorithms can also be performed once a large enough group of users are using the application 200 as described above.

After the analysis, strongest trends 242, key performance indicators (KPIs) 244, and tracking over time 246 are sent to the output module 218 and displayed to the user. For example, predictor variables that meet a 60% or greater threshold are output to users with the output module 218 and flagged as potential causes of their symptoms or KPIs 244. Users are then encouraged to keep tracking to increase the predictive power. Predictor variables meeting a more stringent 90% threshold are flagged as likely causes, or strongest trends 242. Users are then encouraged to talk to their doctors to determine how they can improve their symptoms.

Alternatively, the application 200 can be in communication with external databases and/or medical professionals that can suggest nutrition, medication, or lifestyle changes to improve their symptoms. The medical professionals can review all data collected and analyzed by the application 200 and can adjust dosing of the currently taken drugs or recommend using an alternative drug that would be more effective according to the data collected. Users can review statistics of the outputs by week, month, or year with tracking over time 246.

For example, if a user is taking migraine drugs (such as a daily preventative drug and a drug taken during a migraine), medical professionals can review when the migraine occurred, what medication was taken, and if it was effective. The medical professionals can then determine the efficacy of the drugs and alter the drugs dosage or type taken as necessary.

The application 200 can also include any suitable alarms or notifications that can remind users to input data into the input module 212 or output variable module 214 at certain times of the day or daily. Such notifications can be pushed to the user's mobile devices such as a smart phone, smart watch, tablet, or desktop or laptop computer.

Figure 7:
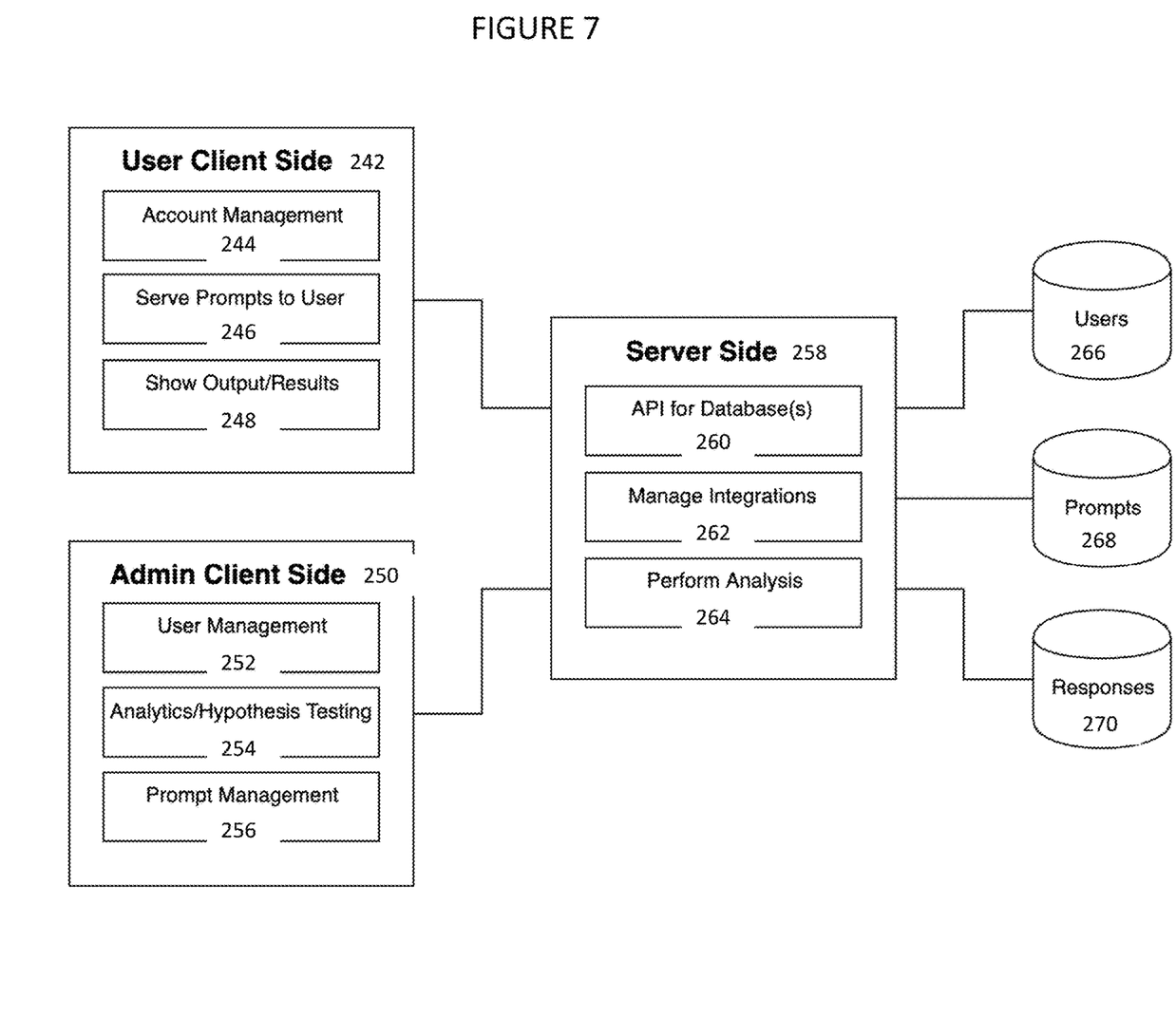
FIG. 7 is a macro-level systems design of the present invention.

FIG. 7 shows a macro-level systems diagram. The User Client Side 242 includes the interactions the software has directly with the user. This includes interactions from native applications (iOS, Android), or web applications (accessed in a browser) and can include account management 244 (sign up, login, password management), serve prompts to user 46, and show output/results 248. The Admin Client Side 250 includes interactions "Admin" level users have access to, such as user management 252, analytics/hypothesis testing 254, and prompt management 256. The Server Side 258 outlines the major functions performed by the server. Application programming interface (API) for databases 260 can be performed. Integrations can be managed 262 including data from other health/nutrition trackers, fitness trackers, wearable devices, etc. Perform Analysis 264 refers to the breakdown represented in FIG. 6. Databases of users 266, prompts 268, and responses 270 can all be in electronic communication with the Server Side 258.

The application 200 can integrate and analyze data (at 262) from outside devices 280 that measure physiological properties of the user and are preferably wearable medical devices. These outside devices 280 can include, but are not limited to, general fitness trackers (FitBits®, Apple® Watch), heartbeat trackers, heart rate trackers, skin temperature trackers, respiratory rate trackers, body posture trackers, eyesight trackers, blood oxygen trackers, glucose level trackers, sleep trackers, body temperature trackers, and skin conductance trackers. Any other suitable physiological data can also be collected. The outside devices 280 can be separate devices or a combination in a single device. Preferably, the outside devices 280 generally provide electrophysiological monitoring. Normally, one would go to a physician after a medical event (such as pain), their physiological conditions would be checked, and a wearable medical device would provide data to see what built up to the medical event to suggest activities not to do to avoid the medical event in the future. Using the application 200 with data from the outside devices 80 allows a user to discover triggers to their disease/mental health that do not necessarily correlate to a medical event that would not be found with just a physician examination and wearable device data alone.

The application 200 can also integrate and analyze data from outside databases 290 (such as database 50), especially having clinical trial data, such as clinics, electronic medical records (EMRs), pharmaceutical companies, private databases, or CROs, further described in U.S. Provisional Patent Application No. 62/878,066. Nearest neighbors can be identified as described above and related study or trial data can be identified in the outside databases 290 to be analyzed. By analyzing additional outside data from the outside databases 290, the application can find others who have similar data as the user and predict an adverse event or triggers to an adverse event.

The application 200 can further combine the analysis of data from outside devices 280 with analysis of outside databases 290 in order to predict adverse events in a user. This allows for a user to know about the likelihood of an adverse event occurring at a later time point so that they can seek appropriate treatment (such as generally having surgery, having a heart bypass or cholesterol removed from arteries, or generally taking medicine) before the adverse event actually happens.

The present invention generally provides for a method of adjusting treatment of a patient, by a patient inputting data about nutrition, medication, lifestyle, symptoms, and user defined metrics in an application, integrating data from outside devices and outside databases, performing an analysis on the data, outputting a result from the data to medical professionals, and the medical professionals adjusting the treatment of the patient based on the data.

The cancer being treated in the present invention can be, but is not limited to, cancer cells associated with adenoid cystic carcinoma, adrenal gland tumors, amyloidosis, anal cancer, appendix cancer, astrocytoma, ataxia-telangiectasia, attenuated familial adenomatous polyposis, Beckwith-Wiedermann Syndrome, bile duct cancer, Birt-Hogg-Dube Syndrome, bladder cancer, bone cancer, brain stem glioma, brain tumors, breast cancer, carcinoid tumors, Carney complex, central nervous system tumors, cervical cancer, colorectal cancer, Cowden syndrome, craniopharyngioma, desmoplastic infantile ganglioglioma, endocrine tumors, ependymoma, esophageal cancer, Ewing sarcoma, eye cancer, eyelid cancer, fallopian tube cancer, familial adenomatous polyposis, familial malignant melanoma, familial non-VHL clear cell renal cell carcinoma, gallbladder cancer, Gardner Syndrome, gastrointestinal stromal tumor, germ cell tumor, gestational trophoblastic disease, head and neck cancer, diffuse gastric cancer, leiomyomatosis and renal cell cancer, mixed polyposis syndrome, pancreatitis, papillary renal cell carcinoma, HIV and AIDS-related cancer, islet cell tumors, juvenile polyposis syndrome, kidney cancer, lacrimal gland tumor, laryngeal and hypopharyngeal cancer, acute lymphoblastic leukemia, acute lymphocytic leukemia, acute myeloid leukemia, B-cell prolymphocytic leukemia, hairy cell leukemia, chronic lymphocytic leukemia, chronic myeloid leukemia, chronic T-cell lymphocytic leukemia, eosinophilic leukemia, Li-Fraumeni Syndrome, liver cancer, lung cancer, Hodgkin lymphoma, Non-Hodgkin lymphoma, Lynch Syndrome, mastocytosis, medulloblastoma, melanoma, meningioma, mesothelioma, Muir-Torre Syndrome, multiple endocrine neoplasia type 1, multiple endocrine neoplasia type 2, multiple myeloma, myelodysplastic syndromes, MYH-associated polyposis, nasal cavity and paranasal sinus cancer, nasopharyngeal cancer, neuroblastoma, neuroendocrine tumors, neurofibromatosis type 1, neurofibromatosis type 2, nevoid basal cell carcinoma syndrome, oral and oropharyngeal cancer, osteosarcoma, ovarian cancer, pancreatic cancer, parathyroid cancer, penile cancer, Peutz-Jeghers Syndrome, pituitary gland tumors, pleuropulmonary blastoma, prostate cancer, retinoblastoma, rhabdomyosarcoma, salivary gland cancer, sarcoma, alveolar soft part and cardiac sarcoma, Kaposi sarcoma, skin cancer, small bowel cancer, stomach cancer, testicular cancer, thymoma, thyroid cancer, tuberous sclerosis syndrome, Turcot Syndrome, unknown primary, uterine cancer, vaginal cancer, Von Hippel-Lindau Syndrome, Wilms tumors, or Xeroderma pigmentosum.

The present invention has several advantages over the prior art. Many current pharmacology related software checks for known high-level interactions between two specific drugs or drug classes. Going beyond that simple check, the present invention checks nearest neighbor patient outcomes when given similar drug combinations. Even if there is no indicated complication, the potential for decrease in efficacy or increase in side effects are considered.

Further, outputs of the present invention are never limited to an quantity of active ingredient, instead, full treatment plans are suggested. This information can be relayed to the patient or used internally for the decision making process. Therefore, the present invention provides a technical effect of providing a treatment plan with dosing of particular cancer therapies/drugs to the patient, as well as providing to the patient the recommended doses. There is potential to maximize a treatment plan while acting in accordance with the suggested use of the drug. Varying treatment plans can be justified if trends suggest preferred outcomes for similar patient profiles. Instead of the present invention being treated as a dosage calculator, it is more so a decision making tool that puts forth all necessary information to the practitioner to make a more informed treatment plans.

The present invention provides advantages to patients because instead of being prescribed cancer therapies/drug combinations at sub optimal and sometimes sub efficacious levels to avoid toxicity and then being dosed up to efficacy while hopefully avoiding toxicity, the present invention can initially dose single or multiple cancer therapies/drugs to a patient at nontoxic and efficacious doses. Thereby, the patient is immediately treated (critical in acute situations such as stroke, seizures, arrhythmia, etc.), while avoiding toxicity.

The present invention provides advantages to physicians because they no longer have to guess at dosing, especially in situations of prescribing multiple interacting cancer therapies/drugs. The platform also takes into account the patient's clinical and physical conditions thereby personalizing the patient's prescription.

The present invention provides advantages to pharmaceutical companies due to avoidance of adverse effects related to either cancer therapies/drugs toxicity or apparent inefficacious use of recommended therapeutics. There are also drug development benefits. The platform can be used to analyze early clinical study data to define a preferred study class for a Phase 3 study. The risk of study failure is greatly reduced.

The present invention provides advantages to insurers by decreasing potential malpractice cases against physicians based on alleged improper prescription practices. Pharmaceutical companies will benefit for the same reasons. More important is that cancer therapies/drugs, especially in multi-prescription situations, can be prescribed to more efficiently be efficacious. Many cancer therapies/drugs are underdosed by physicians afraid of toxicity issues, especially in chronic dosing situations. This results in false negative results and patient failure. Insurance providers are unjustly penalized under those situations. The added cost of the implementation of the platform will be greatly outweighed by the financial benefit and practical benefit to the patient. This removes sometimes unjust prejudice to the pharma brand, adding value to the pharma industry.

The present invention can be useful in dosing any combination of drugs. The drugs can be generally from the classes antihistamines, anti-infective agents, antineoplastic agents, autonomic drugs, blood derivatives, blood formation agents, coagulation agents, thrombosis agents, cardiovascular drugs, cellular therapy, central nervous system agents, contraceptives, dental agents, diagnostic agents, disinfectants, electrolytic, caloric, and water balance, enzymes, respiratory tract agents, eye, ear, nose, and throat preparations, gold compounds, heavy metal antagonists, hormones and synthetic substitutes, oxytocics, radioactive agents, serums, toxoids, and vaccines, skin and mucous membrane agents, smooth muscle relaxants, and vitamins. Some specific combinations of drugs that are most commonly used by people include, but are not limited to, lisinopril and atorvastatin, lisinopril and metformin, amlodipine and lisinopril, alprazolam and amphetamine salt combo, amphetamine salt combo and amphetamine salt combo xr, hydrocodone/acetaminophen and alprazolam, amlodipine and atorvastatin, lisinopril and hydrochlorothiazide, atorvastatin and clopidogrel, atorvastatin and metformin, metformin/lisinopril/atorvastatin, clopidogrel/atorvastatin/lisinopril, glipizide/metformin/lisinopril, atorvastatin/amlodipine/lisinopril, amlodipine/hydrochlorothiazide/lisinopril, carvedilol/atorvastatin/lisinopril, atorvastatin/metoprolol/lisinopril, clopidogrel/metoprolol/atorvastatin, lisinopril/carvedilol/furosemide, and amlodipine/metformin/lisinopril.

Throughout this application, various publications, including United States patents, are referenced by author and year and patents by number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology, which has been used is intended to be in the nature of words of description rather than of limitation.

Obviously, many modifications and variations of the present invention are possible in light of the above teachings. It is, therefore, to be understood that within the scope of the appended claims, the invention can be practiced otherwise than as specifically described.

What is claimed is:

1. A method of dosing cancer therapies, including the steps of:

a healthcare professional collecting and inputting patient data including cancer therapies and drugs to be taken into a database with a central artificial intelligence (AI) stored on computer readable media;

the central AI analyzing the data in view of dosing criteria established based on outside data of clinical trial data from outside databases of clinics, electronic medical records, pharmaceutical companies, private databases, and contract research organizations (CROs), extracting with the AI all features relating variables that effect drug metabolism and creates a model relating dosing to patient condition and effect of cancer therapies and drugs on the condition that effect efficacy and toxicity of all cancer therapies and drugs taken, wherein the variables are age of patient, weight of patient, known side effects of cancer therapies/drugs alone and in combinations with other cancer therapies/drugs, known toxicity range as related to effective dose (ED 50) and dose response points of interest, efficacy ranges, tumor scans, and chronic treatment effect versus acute treatment, identifying with the AI nearest neighbors of persons having similar patient data and/or underwent a treatment plan with similar cancer therapies or drug combinations and identifies related study and trial data with a K-Nearest Neighbor algorithm, comparing with the AI patient data to neighboring patient data with weighting schemes; and calculating with the central AI, for each dosage, classifications with confidence intervals, the generic drug model is ran using the same set of dosages mapped out to the same classifiers used when evaluating context data, the outputs from both models are weighted and combined to determine the optimal dose while simultaneously maximizing therapeutic effect and minimizing adverse effects for the combination of cancer therapies and drugs taken, and displaying the dose in a readable report for a practitioner all in real time.

2. The method of claim 1, wherein said collecting step includes inputting data from a site chosen from the group consisting of clinics, electronic medical records (EMRs), pharmaceutical companies, private databases, and contract research organizations (CROs) to a central artificial intelligence (AI), and inputting data from monitors, EMRs, and insurance information to the central AI.

3. The method of claim 1, wherein said collecting step is further defined as collecting data on symptoms, diagnoses, proposed cancer therapies, drugs, or treatments, fixed demographics, temporal values, genetic components, imaging, and unstructured data.

4. The method of claim 1, wherein said analyzing step includes analyzing data relating to pharmacokinetics, distribution, prior toxicity and efficacy determinations, age, metabolism, and the tumor scans.

5. The method of claim 1, wherein said analyzing step further includes the AI creating a model by extracting any and all variables that effect cancer therapy and drug metabolism and extracting features of how these variables are effected by dosing of additional consumed cancer therapies and drugs.

6. The method of claim 5, wherein the model includes variables of age of patient, weight of patient, known side effects of cancer therapies and drugs alone and in combinations with other cancer therapies and drugs, known toxicity range as related to ED 50, efficacy ranges, and chronic treatment effect versus acute treatment.

7. The method of claim 1, further including the step of dispensing each cancer therapy and drug to the patient.

8. The method of claim 7, further including the step of performing said collecting, analyzing, and determining steps after patient treatment and updated patient scans.

9. The method of claim 1, wherein the cancer therapy is chosen from the group consisting of radiation, surgery, chemotherapy, pain management drugs, and nausea drugs.

10. The method of claim 1, wherein the cancer therapy is chosen from the group consisting of abiraterone acetate, methotrexate, paclitaxel albumin-stabilized nanoparticle formulation, ABVC (doxorubicin hydrochloride, bleomycin, vinblastine sulfate, dacarbazine combination), ABVE (doxorubicin hydrochloride, bleomycin, vinblastine sulfate, etoposide combination), ABVE-PC (doxorubicin hydrochloride, bleomycin, vinblastine sulfate, etoposide, prednisone, cyclophosphamide combination), AC (doxorubicin hydrochloride and cyclophosphamide combination), AC-T (doxorubicin hydrochloride, cyclophosphamide, paclitaxel combination), brentuximab vedotin, ADE (cytarabine, daunorubicin hydrochloride, etoposide combination), ado-trastuzumab emtansine, doxorubicin hydrochloride, fluorouracil, afatinib dimaleate, everolimus, imiquimod, aldesleukin, alemtuzumab, pemetrexed disodium, palonosetron hydrochloride, chlorambucil, aminolevulinic acid, anastrozole, aprepitant, pamidronate disodium, exemestane, nelarabine, arsenic trioxide, ofatumumab, asparaginase *Erwinia chrysanthemi*, bevacizumab, axitinib, azacitidine, BEACOPP (bleomycin, etoposide, doxorubicin hydrochloride, cyclophosphamide, vincristine sulfate, procarbazine hydrochloride, prednisone combination), carmustine, belinostat, bendamustine hydrochloride, BEP (bleomycin, etoposide, cisplatin combination), bevacizumab, bexarotene, tositumomab, I 131 Iodine tositumomab, bicalutamide, carmustine, bleomycin, bortezomib, bosutinib, busulfan, cabazitaxel, cabozantinib-S-malate, CAF (cyclophosphamide, doxorubicin hydrochloride, fluorouracil combination), irinotecan hydrochloride, capecitabine, CAPDX (capecitabine, oxaliplatin combination), carboplatin, carboplatin-taxol combination, carfilzomib, carmustine implant, lomustine, ceritinib, daunorubicin hydrochloride, recombinant HPV bivalent vaccine, cetuximab, chlorambucil, chlorambucil-prednisone combination, CHOP (cyclophosphamide, doxorubicin hydrochloride, vincristine sulfate, prednisone combination), cisplatin, cyclophosphamide, clofarabine, CMF (cyclophosphamide, methotrexate, fluorouracil combination), COPP (cyclophosphamide, vincristine sulfate, procarbazine hydrochloride, prednisone combination), COPP-ABV (cyclophosphamide, vincristine sulfate, procarbazine hydrochloride, prednisone, doxorubicin hydrochloride, bleomycin, vinblastine sulfate combination), dactinomycin, crizotinib, CVP (cyclophosphamide, vincristine sulfate, prednisone combination), ifosfamide, ramucirumab, cytarabine, liposomal cytarabine, dabrafenib, dacarbazine, decitabine, dactinomycin, dasatinib, degarelix, denileu kin diftitox, denosumab, dexrazoxane hydrochloride, docetaxel, doxorubicin hydrochloride liposome, fluorouracil, rasburicase, epirubicin hydrochloride, oxaliplatin, eltrombopag olamine, enzalutamide, EPOCH (etoposide, prednisone, vincristine sulfate, cyclophosphamide, doxorubicin hydrochloride combination), eribulin mesylate, vismodegib, erlotinib hydrochloride, etoposide phosphate, etoposide, everolimus, raloxifene hydrochloride, toremifene, fulvestrant, FEC (fluorouracil, epirubicin hydrochloride, cyclophosphamide combination), letrozole, filgrastim, fludarabine phosphate, fluorouracil, FOLFIRI (leucovorin calcium, fluorouracil, irinotecan hydrochloride combination), FOLFIRI-bevacizumab combination, FOLFIRI-cetuximab combination, FOLFIRINOX (leucovorin calcium, fluorouracil, irinotecan hydrochloride, oxaliplatin combination), FOLFOX (leucovorin calcium, fluorouracil, oxaliplatin combination), pralatrexate, FU-LV (fluorouracil, leucovorin calcium combination), recombinant HPV quadrivalent vaccine, obinutuzumab, gefitinib, gemcitabine hydrochloride, gemcitabine-cisplatin combination, gemcitabine-oxaliplatin combination, gemtuzumab ozogamicin, imatinib mesylate, glucarpidase, goserelin acetate, trastuzumab, topotecan hydrochloride, hyper-CVAD (cyclophosphamide, vincristine sulfate, doxorubicin hydrochloride, dexamethasone combination), ibritumomab tiuxetan, ibrutinib, ICE (ifosfamide, carboplatin, etoposide combination), ponatinib hydrochloride, idarubicin hydrochloride, idelalisib, ifosamide, axitinib, recombinant interferon α-2b, ipilimumab, irinotecan hydrochloride, romidepsin, ixabepilone, ruxolitinib phosphate, palifermin, pembrolizumab, lapatinib ditosylate, lenalidomide, letrozole, leucovorin calcium, leuprolide acetate, vincristine sulfate liposome, procarbazine hydrochloride, mechlorethamine hydrochloride, megestrol acetate, trametinib, mercaptopurine, mesna, temozolomide, mitomycin C, mitoxantrone hydrochloride, MOPP (mechlorethamine hydrochloride, vincristine sulfate, procarbazine hydrochloride, prednisone combination), plerixafor, vinorelbine tartrate, nelarabine, sorafenib tosylate, nilotinib, tamoxifen citrate, romiplostim, ofatumumab, omacetaxine mepesuccinate, pegaspargase, OEPA (vincristine sulfate, etoposide, prednisone, doxorubicin hydrochloride combination), OFF (oxaliplatin, fluorouracil, leucovorin calcium combination), OPPA (vincristine sulfate, procarbazine hydrochloride, prednisone, doxorubicin hydrochloride combination), paclitaxel, PAD (bortezomib, doxorubicin hydrochloride, dexamethasone combination), palifermin, palonosetron hydrochloride, pamidronate disodium, panitumumab, pazopanib hydrochloride, peginterferon α-2b, pembrolizumab, pemetrexed disodium, pertuzumab, plerixafor, pomalidomide, ponatinib hydrochloride, pralatrexate, prednisone, procarbazine hydrochloride, sipuleucel-T, radium 223 dichloride, R-CHOP (rituximab, cyclophosphamide, doxorubicin hydrochloride, vincristine sulfate, prednisone combination), R-CVP (rituximab, cyclophosphamide, vincristine sulfate, prednisone combination), reforafenib, rituximab, romidepsin, ruxolitinib phosphate, talc, siltuximab, sipuleucel-T, sorafenib tosylate, STANFORD V (mechlorethamine hydrochloride, doxorubicin hydrochloride, vinblastine sulfate, vincristine sulfate, bleomycin, etoposide, prednisone combination), sunitinib malate, thalidomide, TAC (docetaxel, doxorubicin hydrochloride, cyclophosphamide combination), temozolomide, temsirolimus, topotecan hydrochloride, toremifene, TPF (docetaxel, cisplatin, fluorouracil combination), trametinib, trastuzumab, vandetanib, VAMP (vincristine sulfate, doxorubicin hydrochloride, methotrexate, prednisone combination), VeIP (vinblastine sulfate, ifosamide, cisplatin combination), vinblastine sulfate, vemurafenib, vincristine sulfate, vincristine sulfate liposome, vinorelbine tartrate, VIP (etoposide, ifosamide, cisplatin combination), vismodegib, vorinostat, XELOX (capecitabine, oxaliplatin combination), ziv-aflibercept, zoledronic acid, QBECO, QBKPN, QBSAU, QBECP, and combinations thereof.

11. The method of claim 1, wherein said collecting step further includes the step of capturing daily activities, intake, and patient symptoms with an application stored on non-transitory computer readable media and determining hidden patterns and effects of the cancer therapies and drugs.

12. The method of claim 11, further including the step of integrating data from outside devices that measure physiological properties of the patient chosen from the group consisting of general fitness trackers, heartbeat trackers, heart rate trackers, skin temperature trackers, respiratory rate trackers, body posture trackers, eyesight trackers, blood oxygen trackers, glucose level trackers, sleep trackers, body temperature trackers, skin conductance trackers, and combinations thereof.

13. The method of claim 1, wherein the patient has cancer chosen from the group consisting of cancer cells associated with adenoid cystic carcinoma, adrenal gland tumors, amyloidosis, anal cancer, appendix cancer, astrocytoma, ataxia-telangiectasia, attenuated familial adenomatous polyposis, Beckwith-Wiedermann Syndrome, bile duct cancer, Birt-Hogg-Dube Syndrome, bladder cancer, bone cancer, brain stem glioma, brain tumors, breast cancer, carcinoid tumors, Carney complex, central nervous system tumors, cervical cancer, colorectal cancer, Cowden syndrome, craniopharyngioma, desmoplastic infantile ganglioglioma, endocrine tumors, ependymoma, esophageal cancer, Ewing sarcoma, eye cancer, eyelid cancer, fallopian tube cancer, familial adenomatous polyposis, familial malignant melanoma, familial non-VHL clear cell renal cell carcinoma, gallbladder cancer, Gardner Syndrome, gastrointestinal stromal tumor, germ cell tumor, gestational trophoblastic disease, head and neck cancer, diffuse gastric cancer, leiomyomatosis and renal cell cancer, mixed polyposis syndrome, pancreatitis, papillary renal cell carcinoma, HIV and AIDS-related cancer, islet cell tumors, juvenile polyposis syndrome, kidney cancer, lacrimal gland tumor, laryngeal and hypopharyngeal cancer, acute lymphoblastic leukemia, acute lymphocytic leukemia, acute myeloid leukemia, B-cell prolymphocytic leukemia, hairy cell leukemia, chronic lymphocytic leukemia, chronic myeloid leukemia, chronic T-cell lymphocytic leukemia, eosinophilic leukemia, Li-Fraumeni Syndrome, liver cancer, lung cancer, Hodgkin lymphoma, Non-Hodgkin lymphoma, Lynch Syndrome, mastocytosis, medulloblastoma, melanoma, meningioma, mesothelioma, Muir-Torre Syndrome, multiple endocrine neoplasia type 1, multiple endocrine neoplasia type 2, multiple myeloma, myelodysplastic syndromes, MYH-associated polyposis, nasal cavity and paranasal sinus cancer, nasopharyngeal cancer, neuroblastoma, neuroendocrine tumors, neurofibromatosis type 1, neurofibromatosis type 2, nevoid basal cell carcinoma syndrome, oral and oropharyngeal cancer, osteosarcoma, ovarian cancer, pancreatic cancer, parathyroid cancer, penile cancer, Peutz-Jeghers Syndrome, pituitary gland tumors, pleuropulmonary blastoma, prostate cancer, retinoblastoma, rhabdomyosarcoma, salivary gland cancer, sarcoma, alveolar soft part and cardiac sarcoma, Kaposi sarcoma, skin cancer, small bowel cancer, stomach cancer, testicular cancer, thymoma, thyroid cancer, tuberous sclerosis syndrome, Turcot Syndrome, unknown primary, uterine cancer, vaginal cancer, Von Hippel-Lindau Syndrome, Wilms tumors, and Xeroderma pigmentosum.

14. The method of claim 1, wherein the drugs are chosen from the group consisting of antihistamines, anti-infective agents, antineoplastic agents, autonomic drugs, blood derivatives, blood formation agents, coagulation agents, thrombosis agents, cardiovascular drugs, cellular therapy, central nervous system agents, contraceptives, dental agents, diagnostic agents, disinfectants, electrolytic, caloric, and water balance, enzymes, respiratory tract agents, eye, ear, nose, and throat preparations, gold compounds, heavy metal antagonists, hormones and synthetic substitutes, oxytocics, radioactive agents, serums, toxoids, and vaccines, skin and mucous membrane agents, smooth muscle relaxants, and vitamins.

15. A logic engine for dosing cancer therapies, comprising an algorithm stored on non-transitory computer readable media for collecting clinical trial data from outside databases of clinics, electronic medical records, pharmaceutical companies, private databases, and contract research organizations (CROs) to establish criteria for dosing cancer therapies/drugs to a single patient and patient data and storing the clinical trial data and patient data in a database, analyzing the patient data in view of criteria established from the clinical trial data with artificial intelligence (AI), extracting with the AI all features relating variables that effect drug metabolism and creates a model relating dosing to patient condition and effect of cancer therapies and drugs on the condition that effect efficacy and toxicity of all cancer therapies and drugs taken, wherein the variables include age of patient, weight of patient, known side effects of cancer therapies/drugs alone and in combinations with other cancer therapies/drugs, known toxicity range as related to effective dose (ED 50) and dose response points of interest, efficacy ranges, and chronic treatment effect versus acute treatment, identifying with the AI nearest neighbors of persons having similar patient data and/or underwent a treatment plan with similar cancer therapies or drug combinations and identifies related study and trial data with a K-Nearest Neighbor algorithm, comparing with the AI patient data to neighboring patient data with weighting schemes, and determining a dose for each cancer therapy/drug, and providing with said algorithm an output in the form of a practitioner readable report all in real time.

16. A method of adjusting treatment of a cancer patient, including the steps of:

a patient inputting data about nutrition, medication, lifestyle, symptoms, and user defined metrics in an application stored on non-transitory computer readable media;

a central artificial intelligence (AI) integrating data from outside wearable medical devices, outside databases of clinical trial data from clinics, electronic medical records, pharmaceutical companies, private databases, and contract research organizations (CROs), and updated patient scans;

performing with the central AI an analysis on the data by the AI extracting all features relating variables that effect drug metabolism and creating a model relating dosing to patient condition and effect of cancer therapies and drugs on the condition that effect efficacy and toxicity of all cancer therapies and drugs taken, wherein the variables include age of patient, weight of patient, known side effects of cancer therapies/drugs alone and in combinations with other cancer therapies/drugs, known toxicity range as related to effective dose (ED 50) and dose response points of interest, efficacy ranges, and chronic treatment effect versus acute treatment, and by the AI identifying nearest neighbors of persons having similar patient data and/or underwent a treatment plan with similar cancer therapies or drug combinations and identifying related study and trial data with a K-Nearest Neighbor algorithm, comparing with the AI patient data to neighboring patient data with weighting schemes;

outputting with the AI a result from the data to medical professionals; and the medical professionals adjusting the treatment of the patient based on the data all in real time.

* * * * *